United States Patent [19]
Burns

[11] Patent Number: 5,458,854
[45] Date of Patent: * Oct. 17, 1995

[54] COLLECTION ASSEMBLY

[75] Inventor: James A. Burns, Elizabeth, N.J.

[73] Assignee: Becton, Dickinson and Company, Franklin Lakes, N.J.

[ * ] Notice: The portion of the term of this patent subsequent to Jan. 24, 2012 has been disclaimed.

[21] Appl. No.: 296,576

[22] Filed: Aug. 26, 1994

Related U.S. Application Data

[63] Continuation-in-part of Ser. No. 60,787, May 12, 1993, Pat. No. 5,384,096.

[51] Int. Cl.$^6$ .................. A61B 5/14; B01L 3/14; B65D 41/18; C12M 1/24
[52] U.S. Cl. ............ 422/102; 128/763; 128/767; 215/295; 215/318; 215/321; 215/354; 220/306; 422/99; 435/288.1; 494/16
[58] Field of Search .................. 128/763–767; 215/211, 214, 217, 224, 228, 223, 295, 321, 353–355, 318; 220/281, 306; 422/99, 102; 435/296; 494/16

[56] References Cited

U.S. PATENT DOCUMENTS

| | | | |
|---|---|---|---|
| 3,136,458 | 6/1964 | Ruetz . | |
| 3,252,446 | 5/1966 | Bateman | 215/295 |
| 3,265,296 | 8/1966 | Mitchell | 494/16 |
| 3,308,039 | 3/1967 | Nelson | 435/296 |
| 3,372,834 | 3/1968 | Ayotte et al. | 220/306 |
| 3,419,179 | 12/1968 | Deuschle et al. | 220/306 |
| 3,430,798 | 3/1969 | Goyet et al. | 215/295 |
| 3,706,306 | 12/1972 | Berger et al. | 128/764 |
| 3,901,400 | 8/1975 | Westfall | 215/224 |
| 3,902,477 | 9/1975 | Gerarde | 215/355 |
| 3,910,444 | 10/1975 | Foster | 215/318 |
| 3,945,525 | 3/1976 | Jones | 215/232 |
| 3,982,651 | 9/1976 | Braun et al. | 220/306 |
| 4,171,057 | 10/1979 | Gach | 215/295 |
| 4,298,129 | 11/1981 | Stull | 215/244 |
| 4,335,823 | 6/1982 | Montgomery et al. | 215/318 |
| 4,390,111 | 6/1983 | Robbins et al. | 215/354 |
| 4,397,318 | 8/1983 | Burns | 128/763 |
| 4,399,920 | 8/1983 | Schwartzbaugh et al. | 215/211 |
| 4,411,163 | 10/1983 | White | 73/864.02 |
| 4,576,185 | 3/1986 | Proud et al. | 128/760 |
| 4,620,549 | 11/1986 | Nugent | 128/763 |
| 4,799,599 | 1/1989 | Hermann | 215/317 |
| 4,804,096 | 2/1989 | Harding | 215/228 |
| 4,805,635 | 2/1989 | Korf et al. | 128/767 |
| 5,288,466 | 2/1994 | Burns | 422/102 |
| 5,384,096 | 1/1995 | Burns | 422/102 |

FOREIGN PATENT DOCUMENTS

| 2041892 | 9/1980 | United Kingdom | 215/295 |
|---|---|---|---|

*Primary Examiner*—James C. Housel
*Assistant Examiner*—Arlen Soderquist
*Attorney, Agent, or Firm*—Nanette S. Thomas

[57] ABSTRACT

The present invention is a collection assembly useful for collecting small quantities of blood. The assembly comprises a container with an integral lip for facilitating collection of the blood and a cap suitable for enclosing the container. The assembly further comprises a sealing arrangement for securing the cap with the container and a cam arrangement for unsecuring the cap from the container.

5 Claims, 8 Drawing Sheets

COLLECTION ASSEMBLY

This application is a continuation-in-part of U.S. Ser. No. 08/060,787, filed on May 12, 1993, now U.S. Pat. No. 5,384,096.

BACKGROUND OF THE INVENTION

1. Field of the Invention

This invention relates to a collection assembly and more particularly to a microcollection container and cap suitable for collecting small quantities of blood from a patient and maintaining the blood in secure fashion for subsequent testing.

2. Description of Related Art

Analytical instrumentation has made it possible to carry out a variety of hematological diagnostic procedures on very small quantities of blood. Because of this, a patient's finger or earlobe, for example, may be punctured and a very small quantity of blood may be rapidly collected into a container for such testing. However, in order to carry out testing and analysis on small quantities of blood, the blood must be rapidly collected prior to any coagulation thereof.

A collection arrangement as described in U.S. Pat. No. 4,397,318, has been provided wherein a cap is configured to fit the top of a microcollection container with the cap having a removable capillary scoop for engaging the puncture site and transferring blood to the container. However, with such an arrangement, if precise positioning is not carried out, capillary action is not initiated or slowed and the collected blood will clot.

Moreover, when a sample is taken with this collection arrangement, blood droplets may be left in and around the top area of the container. When the scoop is removed from the cap and the cap is fitted onto the top of the container, the excess blood may be forced onto the outside surface of the container.

SUMMARY OF THE INVENTION

The present invention is a collection assembly comprising a container and a cap. The cap preferably comprises a top portion, a bottom portion, and an annular skirt extending from the top portion to the bottom portion having an inner surface and an outer surface. The cap further includes an inner inverted skirt portion surrounded by the inner surface of the annular skirt. Most preferably the inner inverted skirt portion is separated from the inner surface of the annular skirt by an annular space. Most preferably, the cap also includes a cam follower positioned on the bottom portion. Desirably, the inside surface of the annular skirt comprises at least one protrusion and the inner inverted skirt portion has a sealing ring. The cap further comprises a rim extending from the outer surface of the annular skirt.

The container preferably comprises an open top portion, a closed bottom portion, a sidewall extending from the top portion to the bottom portion and an open end associated with the top portion having an integral collector. Most preferably the integral collector is a scoop that is the same diameter as the inner diameter of the container so that no air vent is required.

Preferably, the container further includes a cap seating flange associated with the outer diameter of the top portion of the container and an extending annular skirt associated with the bottom portion. Most preferably, a reservoir is positioned within the cap seating flange and at least one lug is located in the reservoir. Preferably, the container also includes a locking ting associated between the integral collector and the cap seating flange.

Preferably, the collection assembly includes means for securing the inner surfaces of the cap to the top portion of the container by the interaction of the protrusions of the cap with the locking ting of the container and the sealing ring of the cap with the inside surface of the top portion of the container. Most preferably, the collection assembly also includes means for unsecuring the cap from the container by a cam arrangement on the cap and container. This cam arrangement assists in substantially reducing fluid splatter from the container when the cap is removed from the container.

In a preferred embodiment of the invention, the cam arrangement includes at least one cam follower positioned on the bottom portion of the cap and at least one cam surface positioned in the cap seating flange of the container. A downwardly rotational force applied to the cap and an upwardly force applied to the container along the longitudinal axis, causes the cam follower and the cam surface to align and the cap to snap-seal to the container by the interaction of the protrusions of the cap with the locking ring of the container and the sealing ting of the cap with the inside surface of the top portion of the container. This action, which may cause an audible-snap, in turn seals the container by compressing the protrusions of the cap against the locking ting of the container and the sealing ring of the cap against the inside surface of the top portion of the container to form a non-permanent lock and to substantially prevent the outer surface of the top portion of the container from making contacting with the inside surface of the cap's annular skirt.

The cap and container are then unsecured in a twist off manner by applying a rotational force to the cap. Most preferably, an upward rotational force is applied to the cap and a downwardly force applied to the container along the longitudinal axis. This causes the cam follower to rise on the cam surface and in turn the cap is unsecured from the container. An important advantage of the present invention is that the rotational force applied to the cap can be bi-directional, that is clockwise or counter-clockwise.

The collection assembly of the present invention is preferably used in micro-centrifuges. However, an extension may be secured and unsecured to the bottom portion of the container. The extension increases the length dimension of the container. With the extension, the container may be compatible with standard clinical centrifuges.

An advantage of the present invention is that any excess fluid on the outside surface of the integral collector is directed downwardly into the cap seating flange. Therefore, radial spray of excess fluid is minimized.

Another advantage of the invention is that the cap may be secured and unsecured to the bottom portion of the container. In particular, the annular space in the cap between the annular skirt and inverted skirt allows the cap to be removably secured with the bottom portion of the container by receiving the annular skirt of the container.

Still another advantage of the invention is that the recessed inverted skirt and the sealing-ring substantially reduces cap contact with fluid collected in the container. Therefore the inner surfaces of the cap may be minimally exposed to fluid collected in the container when the cap is secured to the top portion of the container.

Another advantage of the present invention is that the outer surface of the cap may preferably be configured to substantially limit movement or rolling of the cap or the assembly. This applies whether the cap is positioned with the top portion or bottom portion of the container.

Still another advantage of the present invention is that when the cap is secured to the container, the rim of the cap substantially prevents contamination to the specimen inside the container.

DETAILED DESCRIPTION

Figure 1:
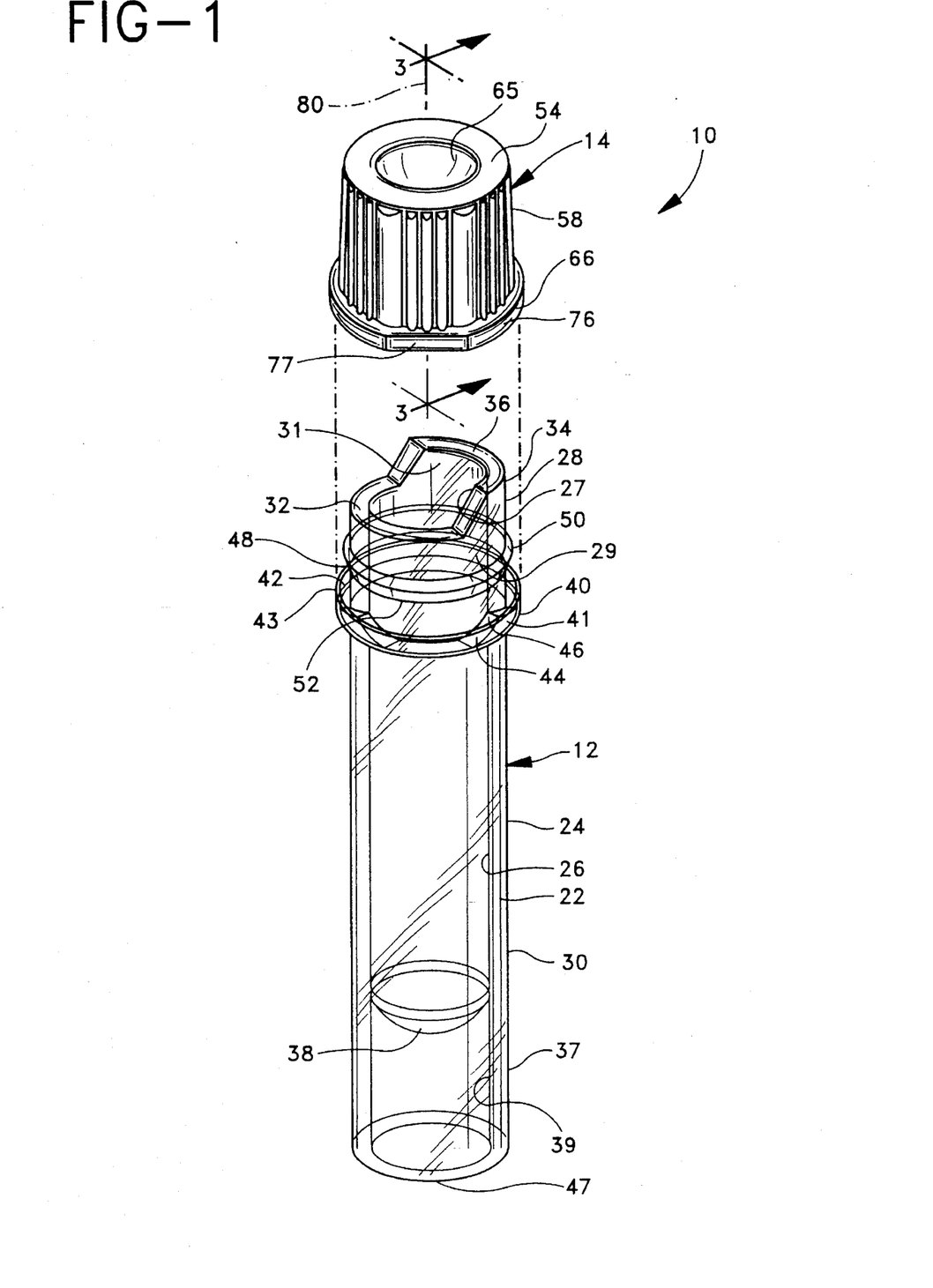
FIG. 1 is a perspective view of the preferred collection assembly illustrating the container with the cap unsecured.

Referring to the drawings in which like reference characters refer to like parts throughout the several views thereof, FIG. 1 illustrates a collection assembly 10 comprising a container 12 and a cap 14.

As illustrated in FIG. 1, container 12 has a sidewall 22 having an outer surface 24 and an inner surface 26. The sidewall extends from an upper portion 28 to a lower portion 30. Upper portion 28 includes an open end 31, an inner surface 27, an outer surface 29 and a top surface 32 having an integral lip portion 34 with a receiving edge 36. Lower portion 30 comprises a closed bottom end 38 and an annular skirt 37 extending from the closed bottom end and outer surface 24 to a bottom edge 47 so as to define a compartment area 39. Annular skirt 37 provides a means for allowing the container to be placed upright on a flat surface.

Upper portion 28 has a cap seating flange 40 positioned around the outer surface of the container which defines a well or trough 42 and an outer surface 41. The cap seating flange has an upper surface edge 43 and a plurality of lugs 44 each having a cam surface 46 in trough 42. Although a container having only one projecting lug is within the purview of the instant invention, a plurality of lugs is preferred. Also, although other shapes and configurations are within the purview of the instant invention, lugs 44 of this embodiment are triangularly shaped.

Figure 2:
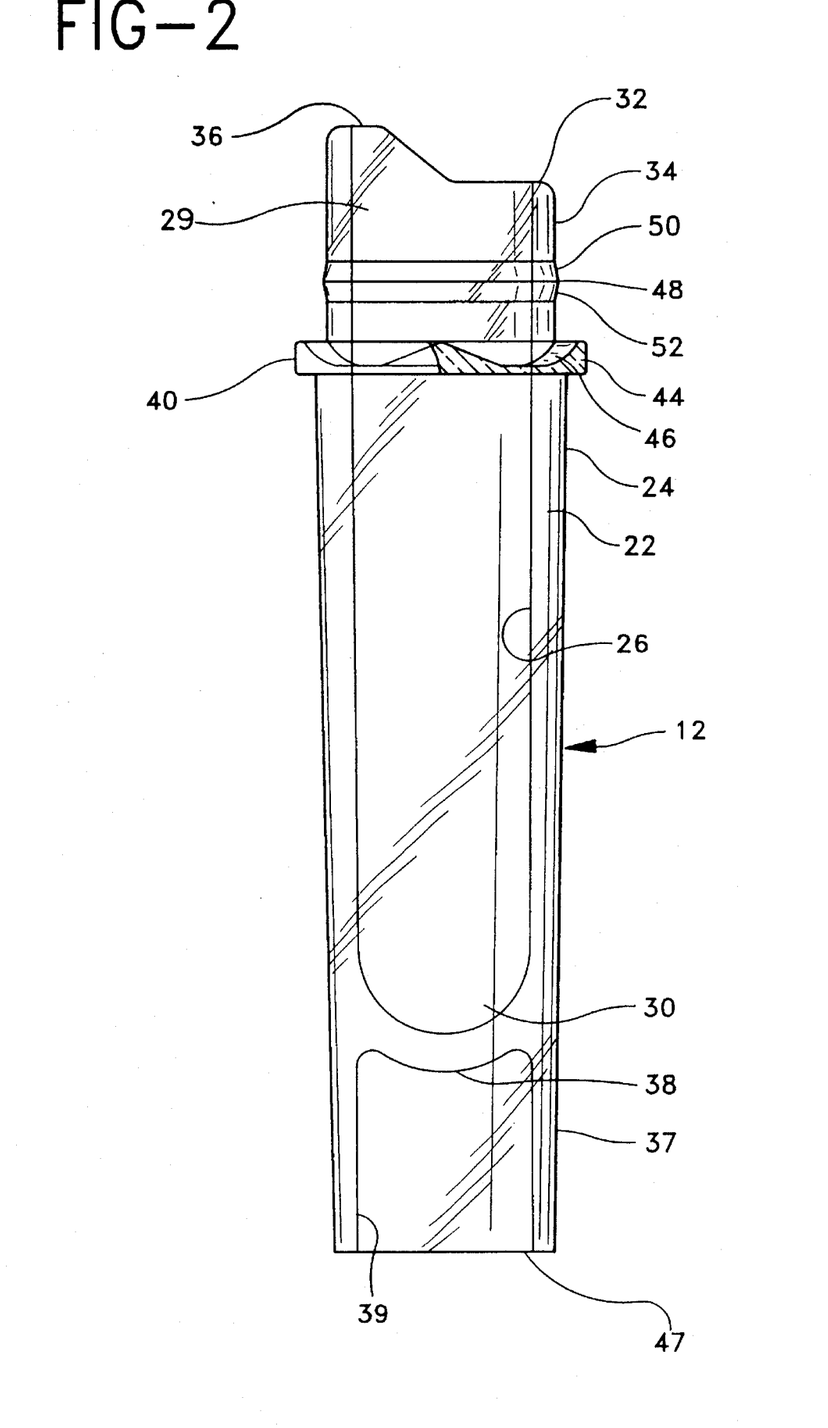
FIG. 2 is a side elevational view of the container of FIG. 1, partially in section of the cam surface area.

As shown in FIG. 2, further positioned on the outer surface of the container on the upper portion is a locking ring 48 positioned between receiving edge 36 of integral lip portion 34 and cap seating flange 40. The locking ring has an upper edge 50 and a lower edge 52.

Figure 3:
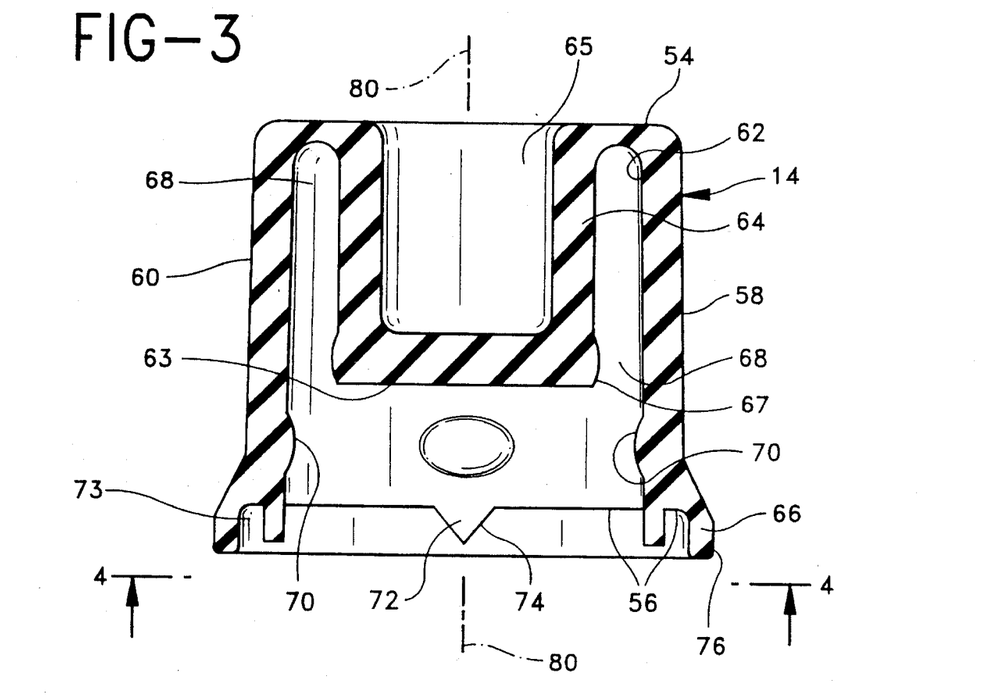
FIG. 3 is an enlarged cross sectional view of the cap of FIG. 1, taken along line 3—3 thereof.

Cap 14 as shown in FIG. 3, has a top surface 54, a bottom stop ledge 56 and an annular outer skirt 58 extending from the top surface to the bottom stop ledge. The annular outer skirt has an outer wall surface 60 and an inner wall surface 62. A shield 66 extends from the outer wall surface of the annular outer skirt and has an outer surface or circumference 76.

As shown in FIG. 3, cap 14 also has an inner annular inverted recessed skirt portion 64 that extends from top portion 54 to a bottom surface 63. The inverted recessed skirt portion defines a compartment or cup area 65 on the top portion of the cap. The inner wall surface of the annular outer skirt and the inner annular inverted recessed skirt are spaced from each other to define an annular space 68. The cap further includes, a plurality of circumferentially spaced protrusions 70 positioned on inner wall surface 62 and a sealing ring 67 positioned on inverted recessed skirt portion 64. Projecting lugs 72 are located on bottom stop ledge 56 wherein each lug comprises a cam follower surface 74. A second annular space 73 is between shield 66 and projecting lugs 72.

Although a cap having only one projecting lug is within the purview of the instant invention, a plurality of lugs is preferred. Also, although other shapes and configurations are within the purview of the instant invention, lugs 72 of this embodiment are triangularly shaped.

Figure 4:
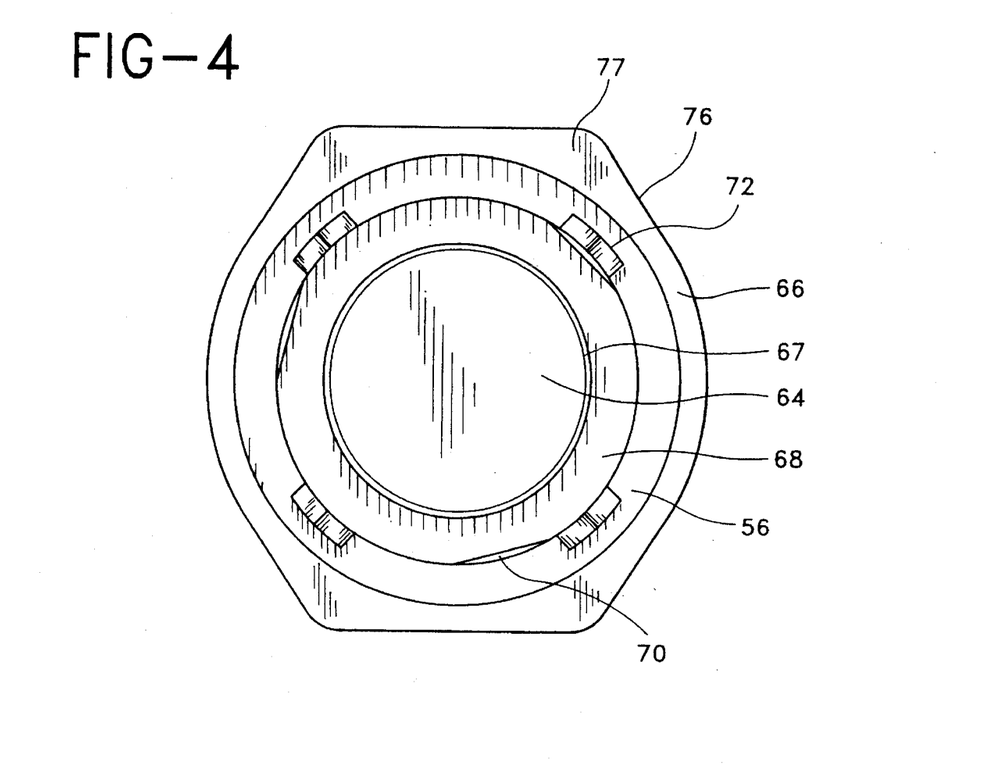
FIG. 4 is a bottom view of the cap of FIG. 1.

As shown in FIG. 4, flats 77 are positioned on the outer surface of shield 66. The flats substantially prevent the cap from rolling and provide a convenient grasping surface for ready removal and placement of the cap on the container. Although a shield with a smooth outer circumference without flats is within the purview of the instant invention, a shield with an outer surface with flats is preferred.

Figure 5:
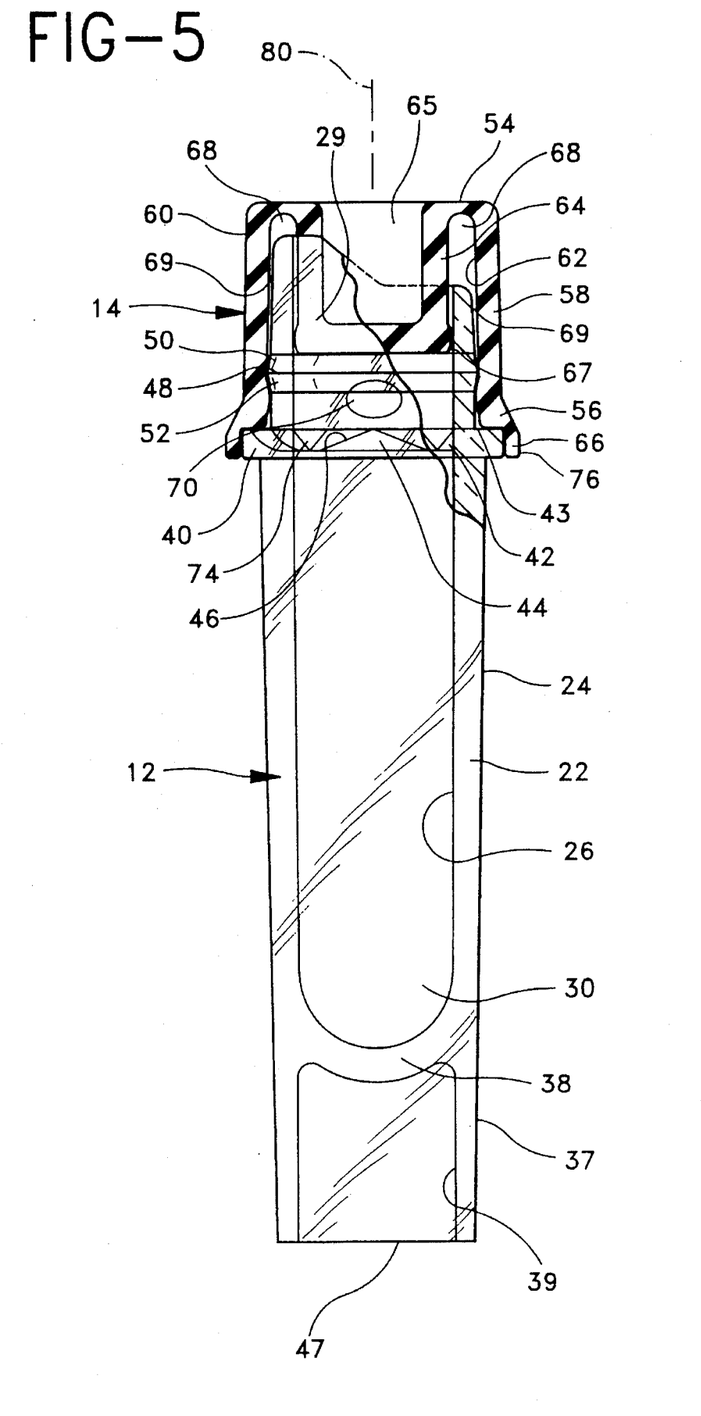
FIG. 5 is a side elevational view, partially in section of the collection assembly of FIG. 1 with the cap secured to the top portion of the container.

As shown in FIG. 5, when cap 14 is removably secured to container 12, space 68 of the cap receives the top portion of the container including the integral lip, wherein the outer protrusions 70 bear against lower edge 52 of locking ring 48 of the container, sealing ring 67 bears against inner surface 27 of the container and cam follower 74 contacts cam surface 46. Shield 66 extends around and not beyond outer surface 41 of cap seating flange 40 and bottom stop ledge 56 abuts with upper surface edge 43 of the cap seating flange 40, so as to form a non-permanent lock and substantially prevent any excess fluid in well 42 of the cap seating flange from spilling out, Any fluid between upper surface edge 43 and bottom stop ledge 56 is substantially directed by shield 66 in a downward direction along the container. Further, any fluid in well 42 is substantially contained by the upper surface edge of the cap seating flange and the bottom stop ledge of the cap.

Cam follower surface 74 and cam surface 46 are configured so that a downwardly rotational force applied to cap 14 about longitudinal axis 80 causes cam follower 74 to contact cam surface 46. Cap 14 is snapped onto the top portion of the container as guided by cam follower surface 74 and cam surface 46. Cap 14 is removably secured to container 12 by protrusions 70 and sealing ring 67 as they bear respectfully against lower edge 52 of the locking ting and inner surface 27 of the container. The position of the protrusions and sealing ring of the cap with the container forms space 69 between outer surface 29 of the top portion of the container and inner wall surface 62 of the cap's annular outer skirt. Therefore, wiping down of any fluid on the container's outer surface is substantially prevented.

The cap is unsecured from the container in a twist-off manner by applying a rotational force about longitudinal axis 80 while holding the container. Rotation of the cap with respect to the container causes cam follower surface 74 to rise on cam surface 46 and in turn the cap is unsecured from the container. The rotational force applied to the cap can be bi-directional, that is clockwise or counter-clockwise.

Figure 6:
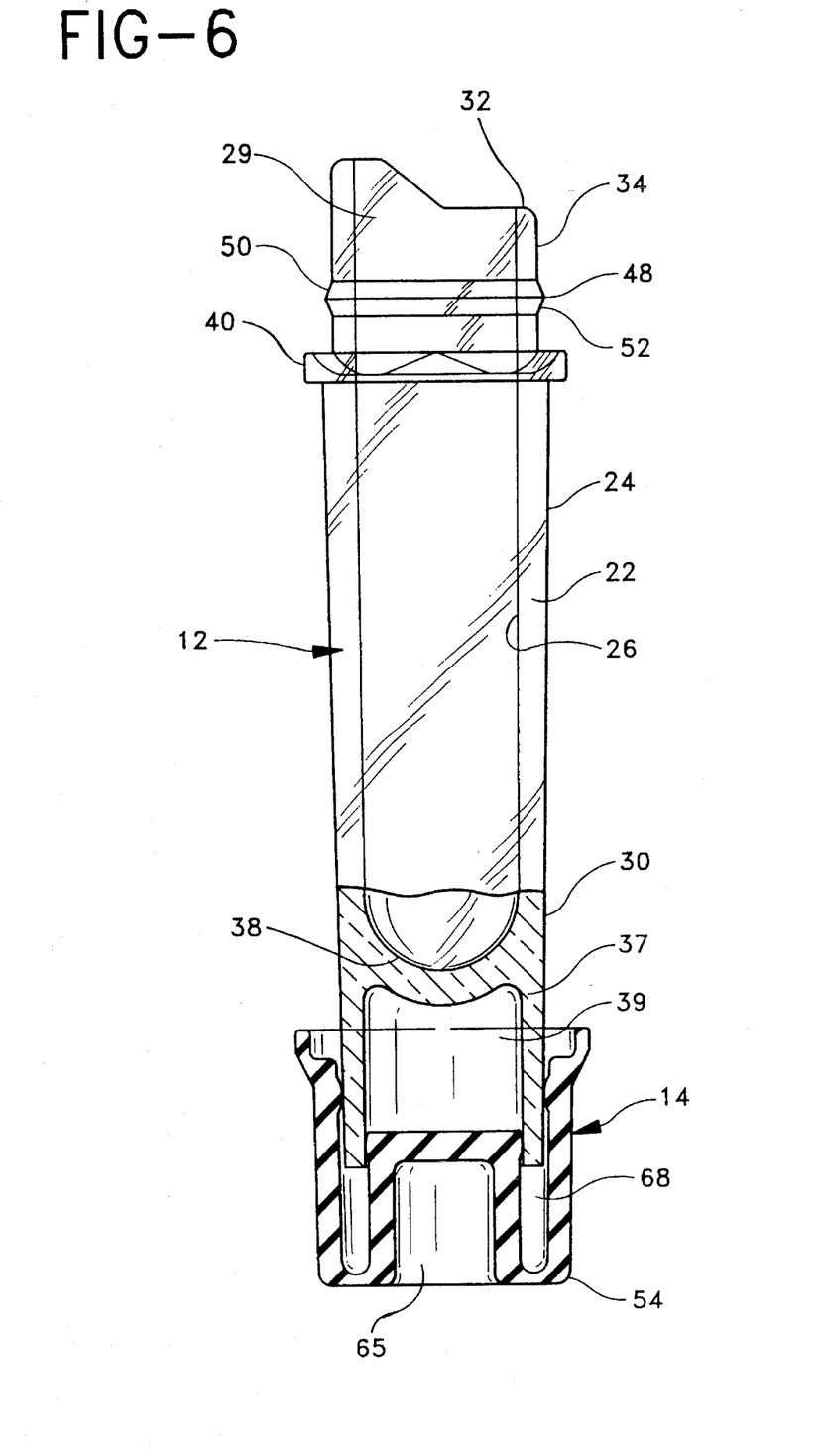
FIG. 6 is a side elevational view, partially in section of the collection assembly of FIG. 1 with the cap removably secured to the bottom portion of the container.

As shown in FIG. 6, cap 14 is readily compatible with skirt 37 on the lower portion of the container. Space 68 of the cap receives the skirt of the container. When the cap is positioned on the bottom of the container during fluid collection, the cap provides a means for allowing the container to be placed upright on a flat surface.

Figure 7:
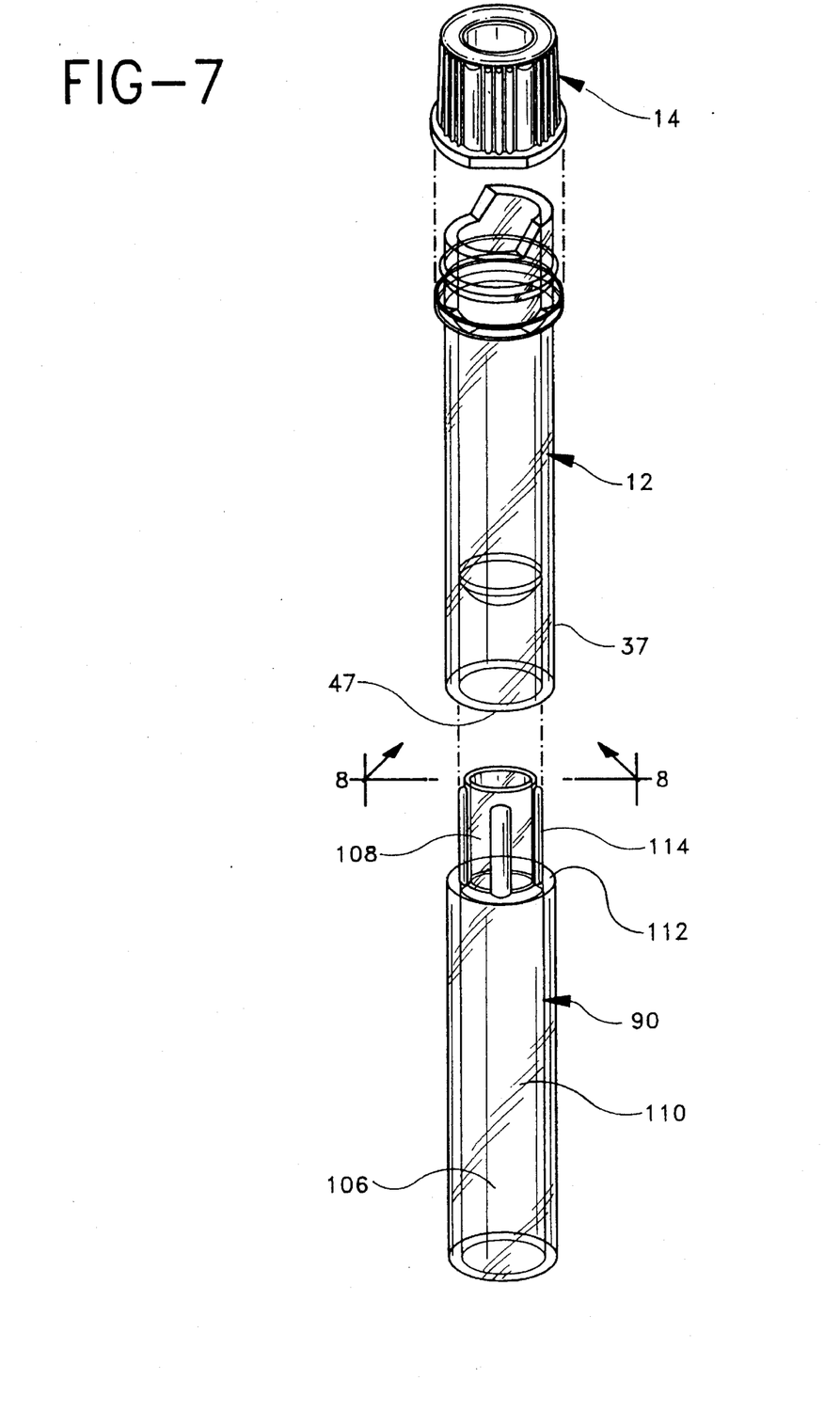
FIG. 7 is a perspective view of the preferred collection assembly of FIG. 1 and an optional extension that may be removably secured to the collection assembly.
Figure 8:
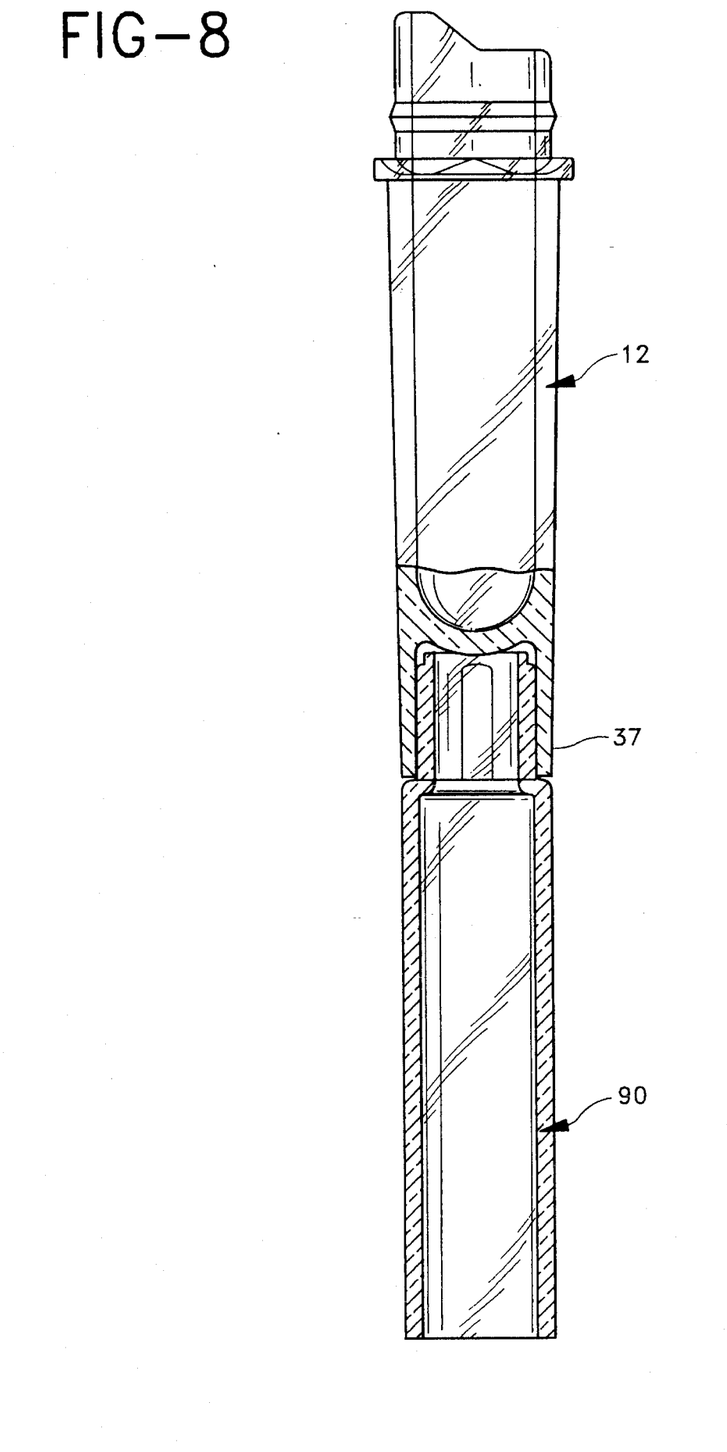
FIG. 8 is a side elevational view, partially in section of the collection assembly of FIG. 7 with an extension removably secured to the bottom portion of the container.

As shown in FIGS. 7 and 8, extension 90 is optionally available to be inserted into skirt 37 on the lower portion of container 12. The extension may be optionally used to make the collection assembly compatible with standard centrifuges or the need for additional space for labeling. Multiple extensions may be used if needed. The extension comprises a tubular body 106 having a neck 108 and a body 110. Neck 108 is less in diameter than body 110 and is separated by a ledge 112. Neck 108 comprises protrusions 114 that bear against compartment area 39 of skirt 37 when neck 108 of the extension is fitted into the skirt of the container. The ledge 108 bears against the bottom edge of the skirt.

Figure 9:
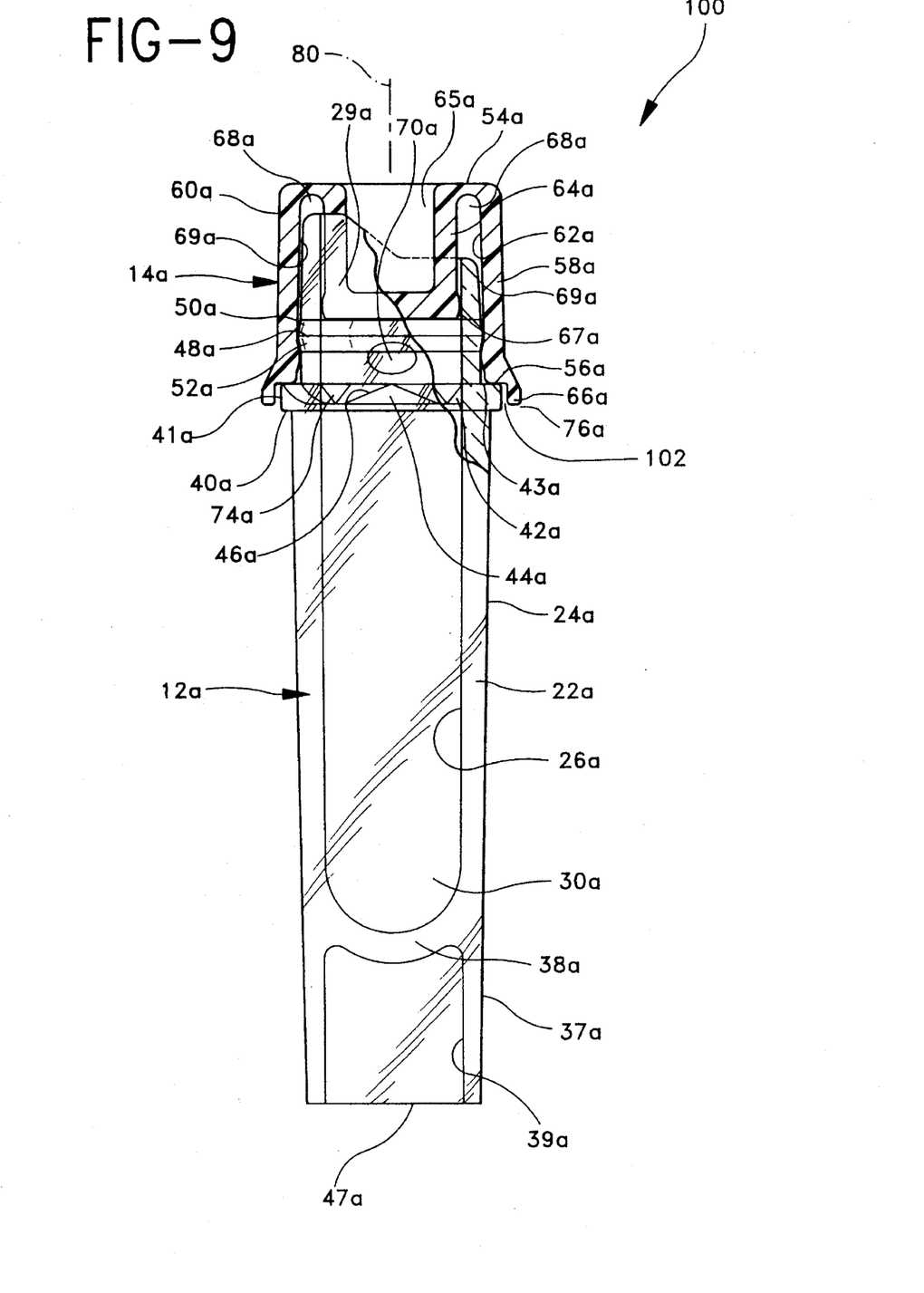
FIG. 9 is a side elevational view, partially in section of the collection assembly similar to FIGS. 1 and 5, illustrating an additional embodiment of the invention with the cap secured to the top portion of the container.

An additional embodiment of the invention, as shown in FIG. 9 includes many components which are substantially identical to the components of FIGS. 1–5. Accordingly, similar components performing similar functions will be numbered identically to those components of FIGS. 1–5, except that a suffix "a" will be used to identify those similar components in FIG. 9.

FIG. 9 shows an alternate embodiment of the invention, a collection assembly 100 comprising a container 12a and a cap 14a. As shown in FIG. 9, the alternate embodiment of the invention comprises a third annular space 102 between the shield 66a and the outer surface 41a of the cap seating flange 40a. When cap 14a is removably secured to container 12a. Further, shield 66a of cap 14a extends around and in length is less than flush with cap seating flange 40a. Therefore, when the capped assembly is centrifuged, the load is on flange 40a and the cap is not loosened.

The collection assembly of the invention may be made of a clear molded thermoplastic material so that the specimen collected may be readily viewed. Representative materials include, for example, polyethylene, polypropylene and polyvinyl chloride. The collection container may incorporate a hydrophilic material or a silicon may be applied to the internal surface thereof for enhancing the flow of blood introduced into the container.

Although is within the purview of the invention to provide caps which are colored to define specific forms of fluid collection containers containing materials for one reason or another or for defining the kind of examination to be conducted on the specimen collected, transparent caps may be provided. Also, it should be noted that the dimensions of the container are such as to provide space for labeling which may be important for identifying the collected specimens.

What is claimed is:

1. A collection assembly comprising:

a cap comprising a longitudinal axis, a top portion, a bottom portion, an annular skirt extending from said top portion to said bottom portion and having an inner surface and an outer surface, an inner inverted skirt portion surrounded by said inner surface of said annular skirt and extending from said top portion toward said bottom portion, an annular space between said inner surface of said annular skirt and said inverted skirt portion, a cam follower extending from said bottom portion of said annular skirt, at least one protrusion positioned on said inner surface of said annular skirt, a sealing ring on said inner inverted skirt portion, and a rim extending from said outer surface of said annular skirt and facing said cam follower wherein a second annular space is provided between said rim and said cam follower; and a container comprising an open top portion, a closed bottom portion, a sidewall extending from said top portion to said bottom portion and having an inner and an outer surface, an integral collector extending from said top portion, a cap seating flange associated with said outer surface of said sidewall, a reservoir positioned within said cap seating flange and at least one lug having a cam surface positioned within said reservoir and a locking ring on said outer surface of said container positioned between said integral collector and said cap seating flange;

wherein said protrusion bears against said locking ring of said container, said sealing ring bears against said inner surface of said top portion of said container and said rim extending around and less than flush with said cap seating flange when said cap is placed over said open top portion of said container.

2. The assembly of claim 1 wherein said cap is removed from said container by applying a bi-directional rotational force to said cap around said longitudinal axis to cause said cam follower of said cap to rise on said cam surface of said container.

3. The assembly of claim 2 wherein said inner inverted skirt portion of said cap is recessed from said bottom portion and said annular skirt of said cap extends beyond said inner inverted skirt portion.

4. The assembly of claim 3 further comprising an annular skirt extending from said closed bottom portion of said container.

5. The assembly of claim 4 wherein said outer surface of said top portion of said container does not contact said inside surface of said annular skirt of said cap when said cap is placed over said open top portion of said container.

* * * * *